United States Patent
Thorley et al.

(10) Patent No.: US 9,604,010 B2
(45) Date of Patent: Mar. 28, 2017

(54) RETRACTABLE SYRINGE NEEDLE

(71) Applicant: UNITRACT SYRINGE PTY LTD, Sydney (AU)

(72) Inventors: Craig Stephen Thorley, Largs (AU); Joseph Hermes Kaal, Raworth (AU); Christopher Rafferty, Raworth (AU); Huw Umberto Wallis, Gladesville (AU); Ernesto Hueso-Monis, Randwick (AU); Kamman Law, Strathfield (AU); Richard Sokolov, Earlwood (AU)

(73) Assignee: Unitract Syringe PTY LTD, Sydney (AU)

( * ) Notice: Subject to any disclaimer, the term of this patent is extended or adjusted under 35 U.S.C. 154(b) by 209 days.

(21) Appl. No.: 14/356,428

(22) PCT Filed: Nov. 9, 2012

(86) PCT No.: PCT/AU2012/001376
§ 371 (c)(1),
(2) Date: May 6, 2014

(87) PCT Pub. No.: WO2013/067588
PCT Pub. Date: May 16, 2013

(65) Prior Publication Data
US 2014/0330217 A1 Nov. 6, 2014

Related U.S. Application Data

(60) Provisional application No. 61/557,792, filed on Nov. 9, 2011.

(51) Int. Cl.
*A61M 5/32* (2006.01)
*A61M 5/315* (2006.01)

(52) U.S. Cl.
CPC ...... *A61M 5/3232* (2013.01); *A61M 5/31515* (2013.01); *A61M 5/3234* (2013.01);
(Continued)

(58) Field of Classification Search
CPC .............. A61M 5/3234; A61M 5/3232; A61M 5/31515; A61M 2005/3231; A61M 2005/3241
(Continued)

(56) References Cited

U.S. PATENT DOCUMENTS 5,180,370 A * 1/1993 Gillespie ............. A61M 5/3202
604/110
5,232,458 A 8/1993 Chen
(Continued)

FOREIGN PATENT DOCUMENTS

CA 2665857 A1 11/2010
CN 1127662 A 7/1996
(Continued)

OTHER PUBLICATIONS

The American Heritage Dictionary definition of "Unitary". Definition 1, available online Jan. 25, 2016 at https://www.ahdictionary.com/word/search.html?q=unitary.*
(Continued)

*Primary Examiner* — Kevin C Sirmons
*Assistant Examiner* — Amber Stiles
(74) *Attorney, Agent, or Firm* — Leydig, Voit & Mayer, Ltd.

(57) ABSTRACT

A retractable needle is provided for a syringe comprising a barrel and a plunger that comprises a portion capable of engaging the retractable needle for retraction. The retractable needle comprises a cannula, a needle body having a plunger-engaging member, at least one aperture and an elongate portion which houses the cannula, the cannula (Continued)

comprising an end which is in fluid communication with the at least one aperture, wherein the at least one aperture is located between the plunger-engaging member and the elongate portion. The positioning of the at least one aperture distal to the plunger-engaging member maximizes the efficiency of fluid delivery.

20 Claims, 18 Drawing Sheets

(52) U.S. Cl.
CPC ............... *A61M 2005/3231* (2013.01); *A61M 2005/3241* (2013.01); *F04C 2270/041* (2013.01)

(58) Field of Classification Search
USPC .......................................................... 604/187
See application file for complete search history.

(56) References Cited

U.S. PATENT DOCUMENTS

| | | | | |
|---|---|---|---|---|
| 5,318,536 A * | 6/1994 | Williams | ............... | A61M 5/322 604/110 |
| 5,431,631 A | 7/1995 | Lu | | |
| 7,604,613 B2 | 10/2009 | Crawford et al. | | |
| 2002/0183699 A1* | 12/2002 | Targell | ................ | A61M 5/3234 604/243 |
| 2004/0006313 A1* | 1/2004 | Chian | ................... | A61M 5/322 604/198 |
| 2004/0267209 A1* | 12/2004 | Kunishige | ............. | A61M 5/322 604/243 |
| 2005/0159705 A1 | 7/2005 | Crawford et al. | | |
| 2006/0106340 A1* | 5/2006 | Goossens | .............. | A61M 5/322 604/110 |

FOREIGN PATENT DOCUMENTS

| | | |
|---|---|---|
| CN | 2650779 Y | 10/2004 |
| CN | 1705496 A | 12/2005 |
| CN | 2836824 Y | 11/2006 |
| DE | 112010000020 T5 | 7/2012 |
| EP | 1426068 A1 | 6/2004 |
| EP | 1445000 A1 | 8/2004 |
| EP | 2371407 A1 | 10/2011 |
| JP | 9-509587 | 9/1997 |
| JP | 2010-531679 | 9/2010 |
| JP | 2010-259718 | 11/2010 |
| TW | 212301 | 9/1993 |
| TW | 312154 | 8/1997 |
| TW | 200610553 | 4/2006 |
| TW | 201039878 A | 11/2010 |
| TW | 201125609 A | 8/2011 |
| WO | WO 91/03269 A1 | 3/1991 |
| WO | WO 91/07198 A1 | 5/1991 |
| WO | WO 94/05356 A1 | 3/1994 |
| WO | WO 95/16478 | 6/1995 |
| WO | WO 2004/035120 A2 | 4/2004 |
| WO | WO 2009/003234 | 1/2009 |
| WO | WO 2011/057334 | 5/2011 |
| WO | WO 2011/075760 A1 | 6/2011 |
| WO | WO 2011/137488 A1 | 11/2011 |

OTHER PUBLICATIONS

European Patent Office, Extended European Search Report in European Patent Application No. 12847776.7 (Apr. 23, 2015).
Chinese Patent Office, Office Action from CN Appln. 201280055139.5, 5 pgs (May 28, 2015).
Japanese Patent Office, Office Action from JP Appln. 2014-540273, 6 pgs (May 26, 2015).
Taiwanese Patent Office, Office Action from TW Appln. 101141881, 24 pgs (Jun. 8, 2015).

* cited by examiner

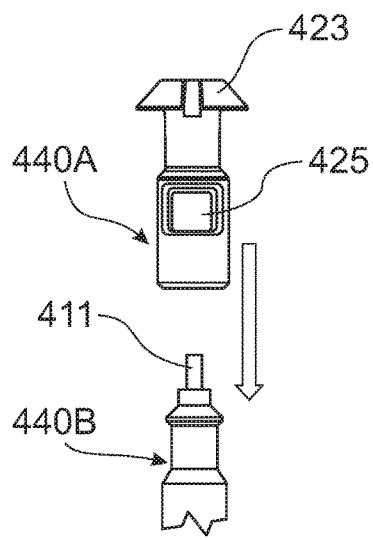
FIG. 5A
FIG. 5B
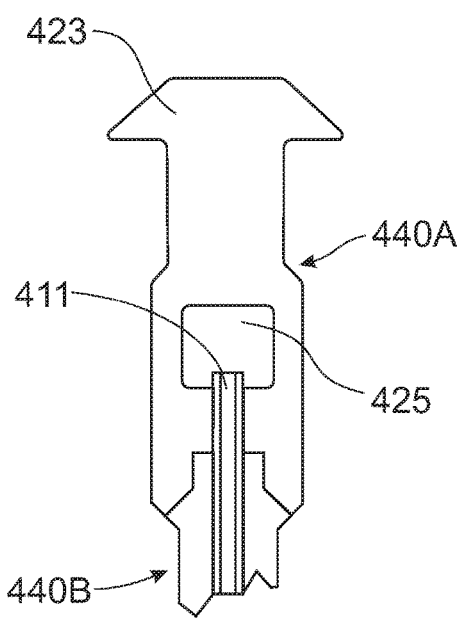
FIG. 5C
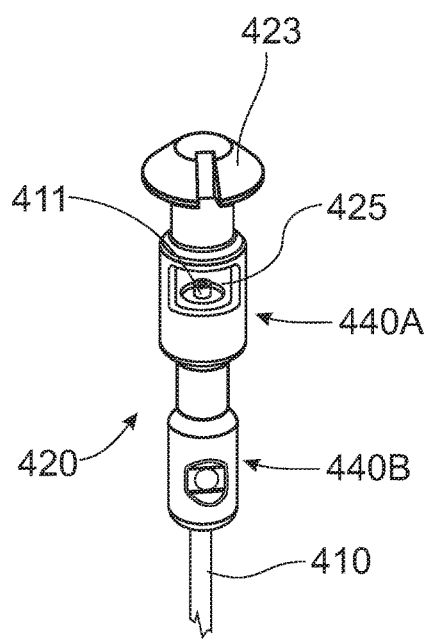

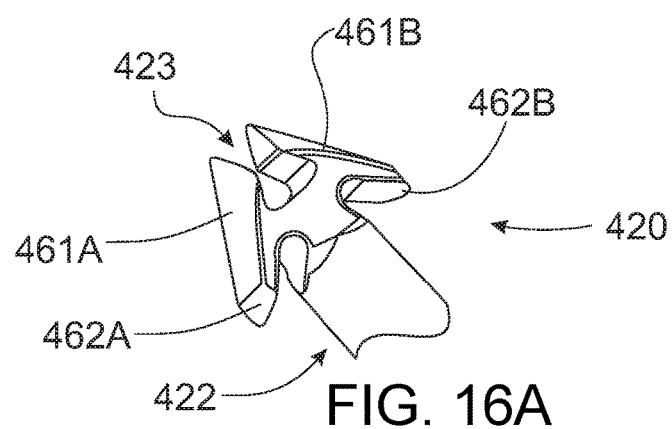
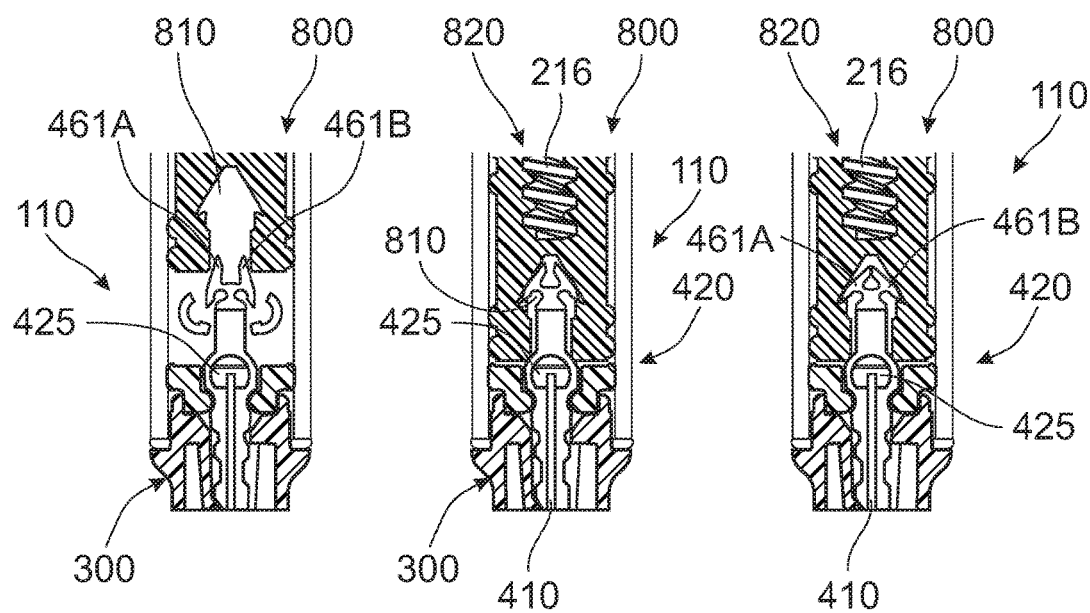
FIG. 16B  FIG. 16C  FIG. 16D

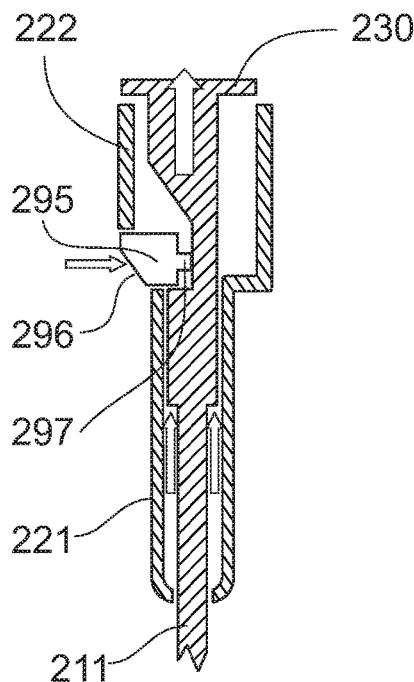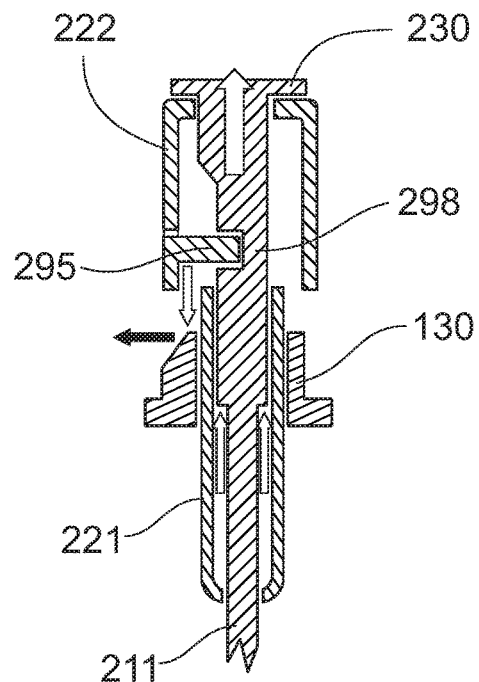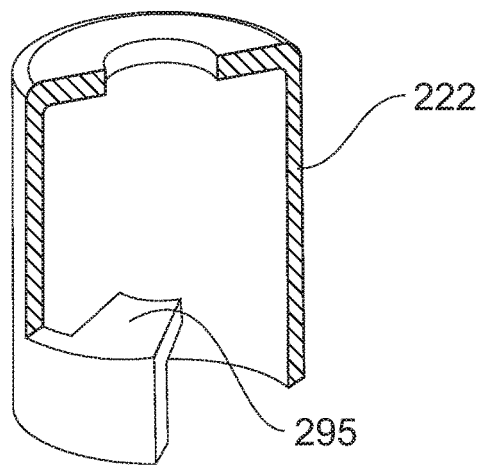
FIG. 17A    FIG. 17B
FIG. 17C

RETRACTABLE SYRINGE NEEDLE

CROSS-REFERENCE TO RELATED APPLICATIONS

This application is a national phase application of International Patent Application No. PCT/AU2012/001376, filed Nov. 9, 2012, which claims priority to U.S. Provisional Application No. 61/557,792, filed Nov. 9, 2011, both of which are incorporated by reference herein in their entireties for all purposes.

FIELD

THIS INVENTION relates to syringes. More particularly, this invention relates to a needle for a retractable syringe.

BACKGROUND

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers. Furthermore, health professionals may be exposed to used syringes which can lead to inadvertent needlestick injuries and possible exposure to infective pathogens or other contaminants.

In response to this problem, retractable syringes have been developed with the aim of preventing syringe re-use and/or needlestick injury by used syringes. Retractable syringes typically comprise a retractable needle as a component of a needle assembly mounted to the syringe barrel, the retractable needle engageable by a plunger or plunger component to enable retraction of the needle.

One problem encountered with many retractable syringes is that the sometimes complicated needle assembly and/or the positioning of the retractable needle relative to the plunger can result in a "dead volume" whereby some of the fluid contents of the retractable syringe fail to be delivered. This can prove costly, particularly in the context of mass-produced, prefilled syringes that deliver expensive pharmaceuticals or vaccines.

It is also a problem that bubbles in the fluid contents are attracted to structures such as the cannula end located in the barrel (i.e., proximal to the user and opposite to the delivery end of the cannula). A user can expel a significant quantity of the fluid contents in trying to expel the bubbles. This is a significant problem in prefilled syringes that are provided with a fixed dosage of fluid contents, in which case the actual fluid amount delivered is substantially less than desired. Additionally, visible fluid bubbles make accurate dose delivery difficult for users to calculate or control as the bubble distracts from the identification of the true dose volume (as may be identified from the start and end positions of the plunger). These problems, among others, exist with retractable syringes known in the drug delivery industry.

SUMMARY

In a broad form, the invention provides an improved retractable needle which facilitates delivery of the fluid contents of a retractable syringe. In a preferred form, the retractable needle comprises an aperture positioned to maximize the efficiency of fluid delivery. The retractable needle having an aperture eliminates the visual "dead volume" associated with many retractable syringes. Furthermore, the retractable needle having an aperture permits accurate dose control by users by eliminating the visual bubble commonly found in, the known syringes. The improved retractable needle of the present invention addresses these problems while incorporating integrated safety features highly desired by users of such needles.

In one aspect, the invention provides a retractable needle for a syringe comprising a barrel and a plunger comprising a portion capable of engaging the retractable needle for retraction of the retractable needle, said retractable needle comprising a cannula, a needle body having a plunger-engaging member, at least one aperture and an elongate portion which houses at least part of the cannula, the cannula comprising an end which is in fluid communication with the at least one aperture, wherein the at least one aperture is located between the plunger-engaging member and the elongate portion.

Suitably, the at least one aperture is in fluid communication with fluid contents of the barrel when in use.

In another aspect, the invention provides a needle assembly mountable to a barrel of a syringe, the needle assembly comprising the retractable needle of the first aspect.

Suitably, the needle assembly further comprises a needle seal. Suitably, the needle assembly is mountable to a syringe barrel adapter. Preferably, the barrel adapter comprises a body that includes a needle portion and a barrel-engaging portion.

The barrel may further comprise a collar. In certain embodiments, the barrel adapter is adhered to a needle end of the barrel and the collar is adhered to a plunger end of the barrel. In some embodiments, the barrel adapter and the collar are adhered to the barrel simultaneously or sequentially.

In yet another aspect, the invention provides a retractable syringe comprising the needle assembly of the second aspect, a barrel and a plunger comprising a portion capable of engaging the plunger-engaging member of the retractable needle.

Typically, the at least one aperture extends transversely through the retractable needle body relative to a longitudinal axis of the cannula.

Suitably, the at least one aperture of the retractable needle is positioned so that it minimizes "dead space" in the syringe barrel. Positioning of the aperture is preferably such that at least a portion of, or the entire aperture, is located between the portion of the plunger capable of engaging the plunger-engaging member and the end of the cannula. This thereby improves the efficiency of delivery of fluid contents of the syringe.

In one embodiment, the cannula end may extend into a space defined by the at least one aperture. In another embodiment, the cannula end may terminate at a periphery of the at least one aperture without extending into the space defined by the at least one aperture. In yet another embodiment, the cannula end may terminate within the elongate body. Suitably, the cannula end of this embodiment is in fluid communication with a bore which is in fluid communication with the aperture.

In one embodiment, the retractable needle is unitary. In one form, the cannula and the needle body are co-moulded to form the unitary retractable needle. In another embodiment, the retractable needle body and the cannula are separate components of the retractable needle. In one particular embodiment, the retractable needle body is an over-mould of the cannula. In another particular embodiment, the retractable needle body comprises a first body member and a second body member. Preferably, prior to assembly the first body member comprises the cannula and the second body member comprises the plunger-engaging member, or vice versa.

The retractable needle may further comprise one or a plurality of mating portions that engage complementary mating portions of the needle seal. The mating portions may be ribs and the complementary mating portions of the needle seal may be grooves, or vice versa. When the retractable needle and needle seal are assembled, engagement between the respective complementary mating portions prevents movement of the retractable needle proximally (i.e., towards the user) such as when piercing the skin or a vial closure. Suitably, the retractable needle is capable of engaging the needle seal.

Suitably, the plunger comprises a plunger member, a plunger outer, a controlling member and biasing means, such as a spring, wherein the plunger member, the plunger outer and the controlling member co-operate to retain the biasing means in an initially energized state. Suitably, release of the biasing means from the initially energized state facilitates retraction of the retractable needle when engaged with the plunger member. In one embodiment, the biasing member is a spring. According to this embodiment, the spring is initially compressed, whereby decompression of the spring facilitates retraction of the retractable needle when engaged with the plunger member.

Suitably, the plunger further comprises a plunger seal. Preferably, the plunger seal is coupled to the plunger member. In one embodiment, the plunger seal comprises the portion of the plunger capable of engaging the plunger-engaging member of the retractable needle.

Other preferred objects and embodiments of the invention include providing an improved plunger that displays less wobble and/or tilt during axial movement, an improved coupling between plunger seal and plunger, an improved spring retaining system and/or an improved barrel, although without limitation, thereto.

In particular embodiments, the invention provides a plunger wherein:
 (a) the plunger further comprises a connector that couples the plunger member to the plunger seal;
 (b) the plunger member comprises a plunger seal engaging member that comprises flexible members comprising edged portions that engage the plunger seal;
 (c) the plunger outer and controlling member are releasably engaged by a release member to initially compress a spring, which release member is laterally moveable to facilitate release of said plunger outer and said controlling member to thereby facilitate decompression of said spring;
 (d) the plunger further comprises a locking system whereby said plunger outer comprises an arm that engages said plunger member after retraction of the plunger member and needle engaged therewith; and/or
 (e) the plunger further comprises a locking system whereby arms of the controlling member engage the plunger outer after retraction of the plunger member and needle engaged therewith.

Optionally, the plunger member further comprises a flange that abuts the plunger seal to thereby reduce tilt or wobble of the plunger member in use.

In yet another embodiment, the invention provides a barrel for a syringe, wherein the barrel comprises an elliptical cross-sectional shape. Suitably, the barrel facilitates threading of a plunger member to a plunger seal. In one particular embodiment, the plunger seal comprises an elliptical cross-sectional shape.

In a further embodiment, the invention provides a spring retainer for a retractable syringe, said spring retainer comprising an inner member and an outer member that co-operate to releasably retain said spring in an initially compressed state, whereby release of the inner member and the outer member facilitates spring decompression to thereby facilitate needle retraction.

Suitably, the syringe of the aforementioned aspects and embodiments is a retractable pre-filled syringe.

In this context, "pre-filled" means that the retractable syringe contains deliverable fluid contents before supply to, or purchase or operation by, the user. Accordingly, a pre-filled syringe obviates the step of the user filling the syringe with fluid contents.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein: ,
FIGS. 5A, 5B and 5C show another embodiment of a retractable needle;
FIGS. 16A, 16B, 16C and 16D show another embodiment of a plunger-engaging member of a retractable needle
FIGS. 17A, 17B, and 17C show embodiments of a lateral release system for a plunger outer, controlling member and compressed spring.

DETAILED DESCRIPTION

Figure 1:
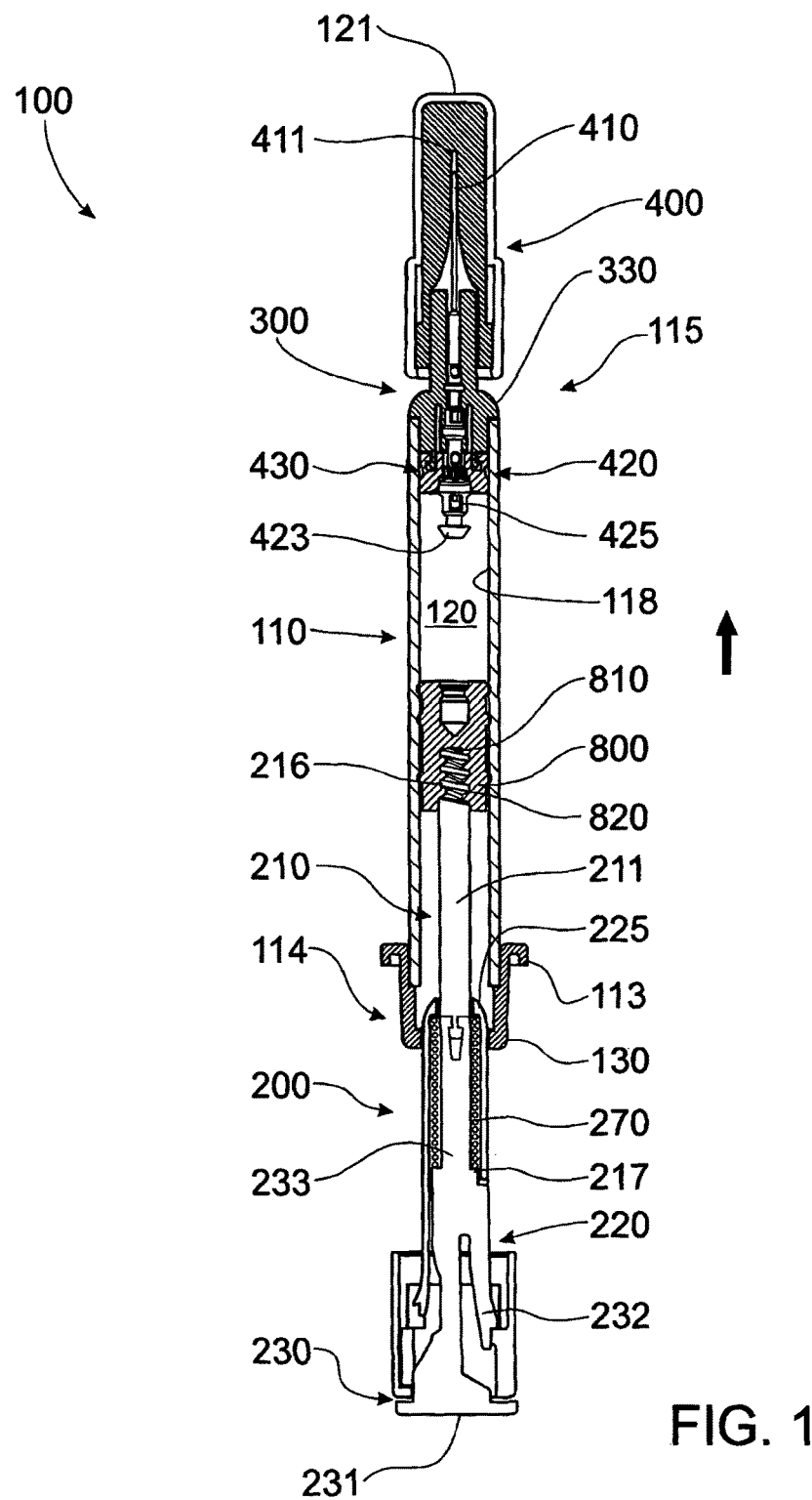
FIG. 1 shows an embodiment of a retractable syringe.

Referring to FIG. 1, an embodiment of retractable syringe 100 comprises barrel 110 having plunger end 114 and needle end 115. Barrel 110 is substantially cylindrical in shape and is preferably formed of glass. At plunger end 104 of barrel 110 is located collar 113 having release ring 130. Collar 113 may be mounted, glued, fitted or integrally formed with barrel 110. In embodiments where barrel 110 is formed of glass, collar 113 is glued or otherwise adhered to barrel 110. In alternative embodiments where barrel 110 is formed of plastic or other mouldable material, collar 113 is formed integrally with barrel 110 (e.g by moulding). Release ring 130 may be mounted or otherwise fitted to barrel 110, or may be co-moulded with collar 113 and barrel 110. Typically, syringe 100 is supplied with protective cover 121 over cannula 410 to protect cannula tip 411. At needle end 105 of barrel 110 is mounted barrel adapter 300 and retractable needle 400 comprising cannula 410, needle body 420 and needle seal 430. Syringe 100 further comprises plunger 200 comprising plunger seal 800 mounted thereto. Barrel 110 further comprises inside wall 118 which, together with needle body 420, needle seal 430 and plunger seal 800 defines fluid space 120 inside barrel 110.

As shown in FIG. 1, in use plunger 200 is movable axially into fluid space 120 in the direction of the solid arrow to facilitate delivery of fluid contents of retractable syringe 100. In a preferred embodiment, fluid space 120 is prefilled with fluid contents to be delivered by retractable syringe 100. In this context, by "prefilled" is meant that retractable syringe 100 is provided to the user filled with deliverable fluid contents without the need for the user to fill barrel 110 with the fluid contents.

Figure 2:
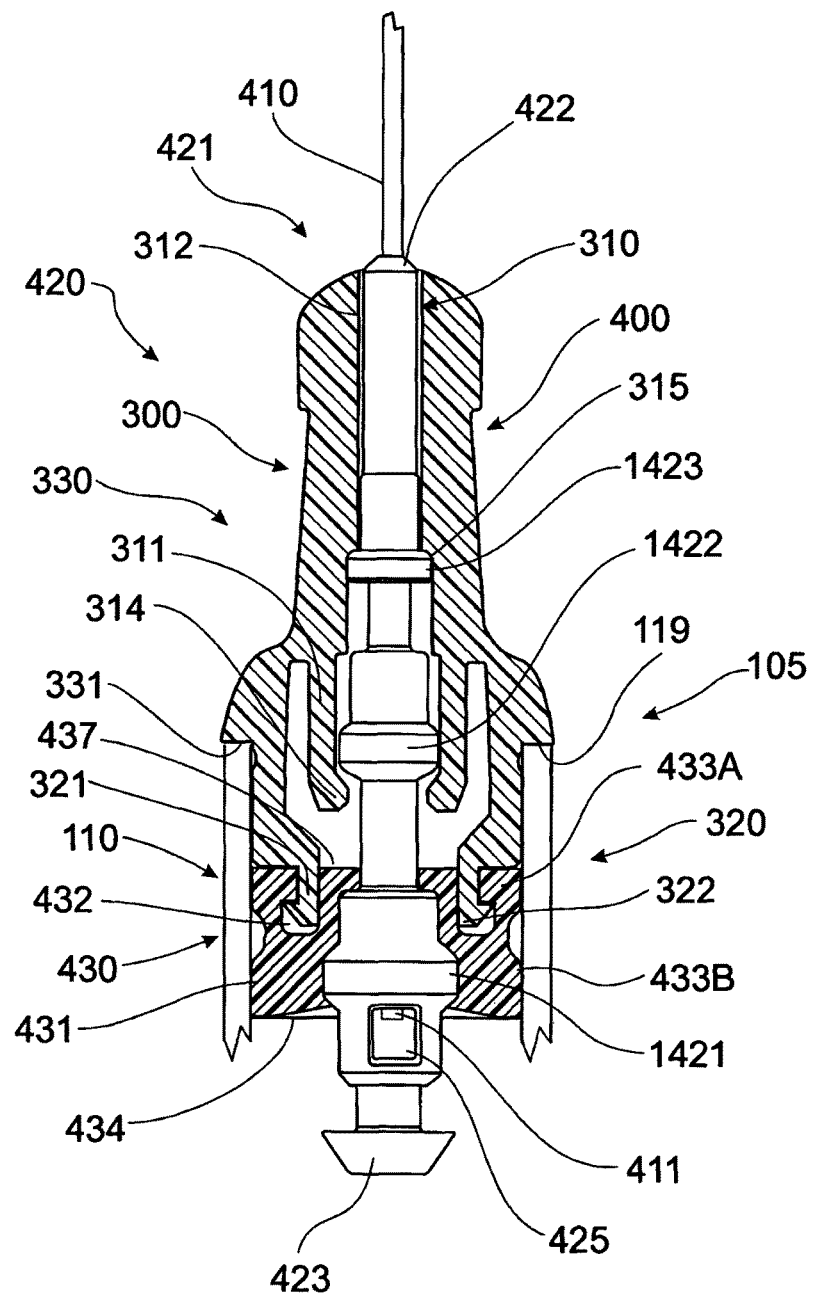
FIG. 2 shows an embodiment of a needle assembly and adapter mounted to a barrel of a retractable syringe.

Referring to FIG. 1 and FIG. 2, barrel adapter 300 comprises needle portion 310 that comprises spigot 311 and needle aperture 312; needle seal-engaging member 320 that comprises mounting ring 321 having annular barb 322 and shoulder 323; and barrel-engaging portion 330 that comprises circumferential shoulder 331 which bears against rim 119 of barrel 110. Retractable needle 400 comprises cannula 410 having end 411 and needle body 420 comprising elongate portion 421 and proximal end 422 that comprises plunger-engaging member 423. Aperture 425 extends transversely through retractable needle body 420 relative to a longitudinal axis of cannula 410 and is in fluid communication with the fluid contents of barrel 110. In some embodiments such as shown in FIG. 2 proximal end 422 comprises waist or increased diameter portion 1421 distal to aperture 425.

Needle body 420 further comprises proximal annular boss 1422 which is engaged by hook end 314 of spigot 311 to assist releasable coupling of retractable needle 400 and barrel adapter 300. Needle body 420 further comprises distal annular boss 1423 which releasably engages internal shoulder of 315 of barrel adapter 300 to thereby prevent distal movement of retractable. needle 400. Needle seal 430 comprises body 431 having barb seat 432 and sealing ribs 433A, 433B that facilitate a fluid seal against inside wall 118 of barrel 110 and edge 434.

As also best seen in FIG. 2, barb seat 432 accommodates annular barb 322 of mounting ring 321 of barrel adapter 300 to thereby couple needle seal 430 to barrel adapter 300. Spigot 311 bears against annular boss 1422 needle body 420 and cannula 410 extends through needle aperture 312 so that cannula tip 411 is free for delivery of fluid contents once cover 121 is removed. This arrangement renders needle seal 430 immobile throughout the use of retractable syringe 100. According to this embodiment, collar 113 comprising releasing ring 130 and barrel adapter 300 are plastic components that are glued or adhered to glass barrel 110.

In one form, barrel adapter 300 and collar 113 are sequentially glued or adhered to glass barrel 110, each gluing or adhesion step followed by a UV curing step. In an alternative form, barrel adapter 300 and collar 113 are simultaneously glued or adhered to barrel 110, followed by a UV curing step. Retractable needle 400 is then mounted to barrel adapter 300.

In the embodiment of retractable needle 400 shown in FIG. 2, cannula end 411 is "sub-flush" to edge 434 of seal 430 to eliminate bubbles and minimize dead space. More particularly, when plunger seal 800 engages plunger-engaging member 423, the positioning of cannula end 411 distal to edge 434 of seal (i.e., distal from the user) means that there is no fluid-containing volume distal to cannula end 411 that can form a dead-space. Aperture 425 in needle body 420 also improves access of fluid contents to cannula end 411, thereby minimizing wastage of fluid contents through failure to enter cannula 410.

Another advantage of aperture 425 relates to air bubbles which typically collect at cannula end 411. In prior art syringes a user may try and expel the visible air bubbles by expelling fluid contents before injection. This can result in losses of fluid contents to the extent that the delivered volume is substantially less than the original volume provided with prefilled syringe 100. By placing cannula end 411 more distal in syringe 100 and less visible to the user, the user is less inclined to persist with removing bubbles and wasting fluid contents. In the embodiment shown in FIG. 2, aperture 425 is located at a position proximal to needle seal 430 (i.e., proximal to the user), but in other embodiments aperture 425 could be located partially or completely within needle seal 430.

Figures 3A, 3B, 3C:
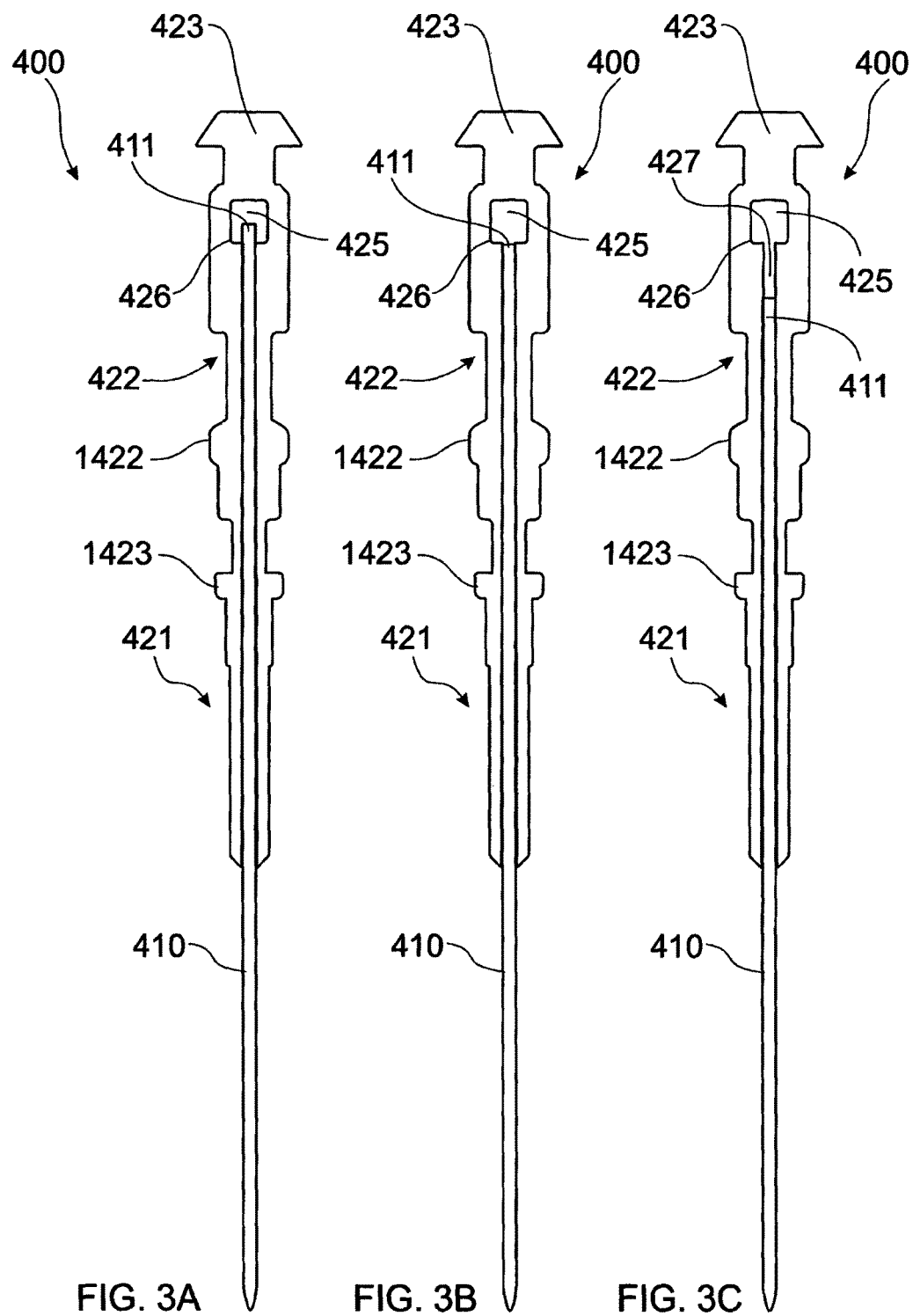
FIG. 3A, FIG. 3B and FIG. 3C shows embodiments of a retractable needle.

It will also be appreciated that the positioning of cannula end 411 relative to aperture 425 can be varied. In the embodiment shown in FIGS. 1, 2 and 3A, cannula end 411 extends beyond, or proximal to, distal ledge 426 into aperture 425. Alternatively, as shown in FIG. 3B, cannula end 411 could extend no further than, or terminate at, distal ledge 426 of aperture 425. In another embodiment shown in FIG. 3C, cannula end 411 terminates short of, or distal to, distal ledge 426 of aperture 425. In this embodiment, bore or channel 427 could provide fluid communication between cannula end 411 and aperture 425.

The invention also contemplates various embodiments of needle body 420, particularly in relation to the way in which needle body 420 and cannula 410 are assembled or manufactured. Broadly, needle body 420 and cannula 410 may be separate components or may be a preformed unitary structure such as by co-moulding or dual-shot assembly or manufacturing processes.

Figure 4A:
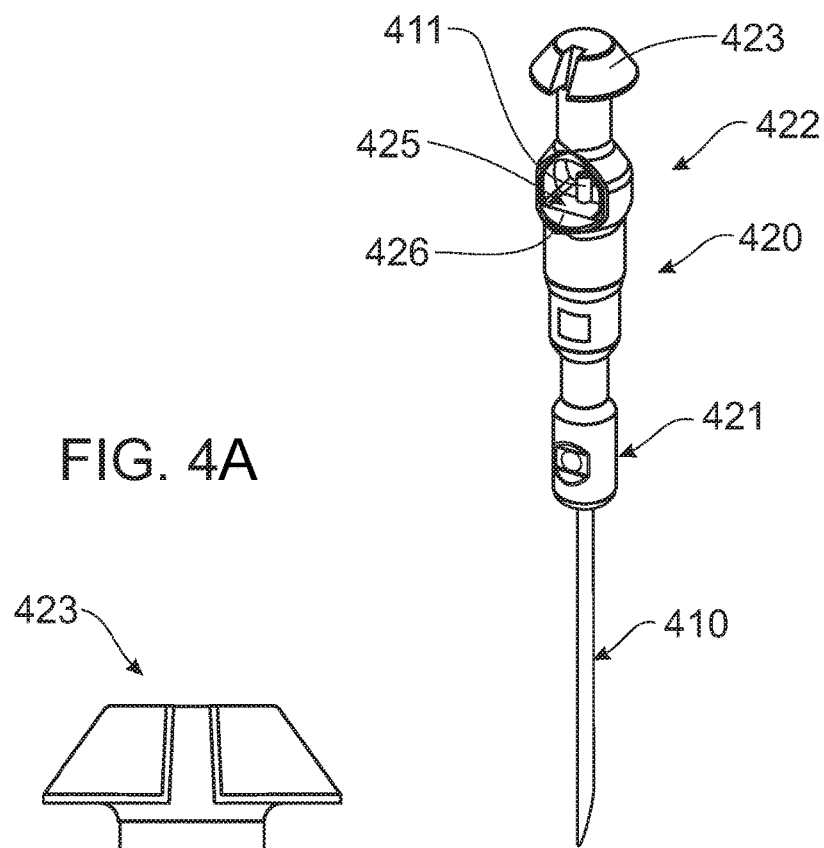
FIGS. 4A and 4B show another embodiment of a retractable needle.
Figure 4B:
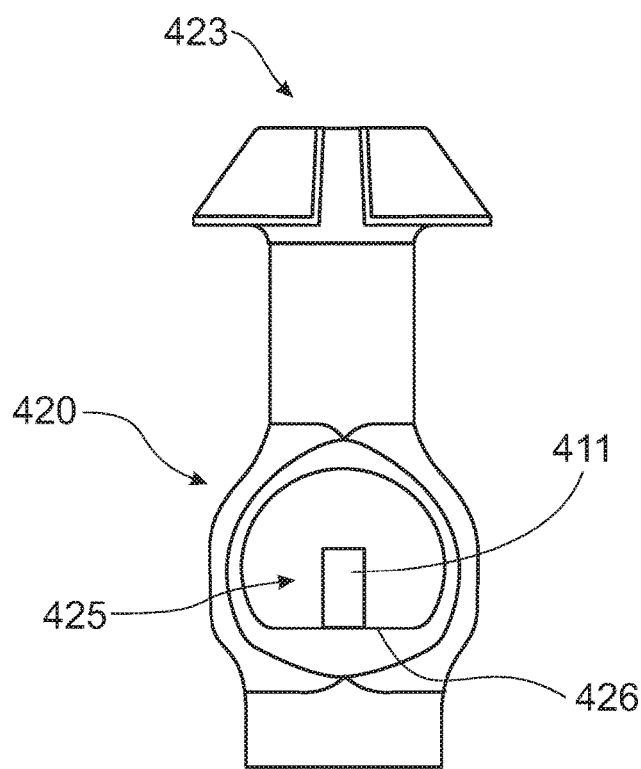

In an embodiment shown in FIG. 4, needle body 420 is an "overmould" to cannula 410, which provides a relatively quick, one step assembly process. In an alternative embodiment shown in FIG. 5, needle body 420 comprises separate body members 440A, 440B which are adhered by glue. First needle body member 440A is an "overmould" to cannula 410, while second needle body member 440B comprises plunger-engaging member 423. Second needle body member 440B engages needle seal 430 (not shown). This embodiment should reduce dead space as there is no need for aperture 425 to support cannula end 411 during moulding.

Figure 6A:
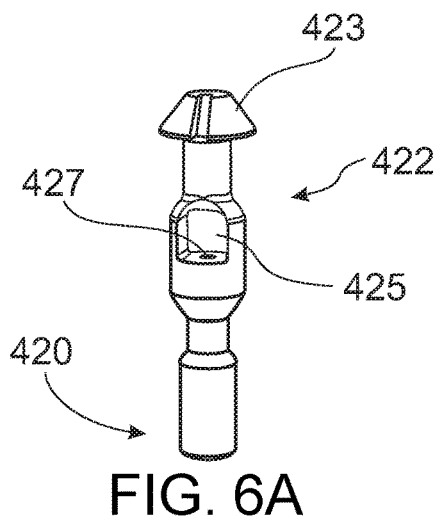
FIGS. 6A, 6B and 6C show another embodiment of a retractable needle mounted to an embodiment of a barrel adapter and needle seal.
Figure 6B:
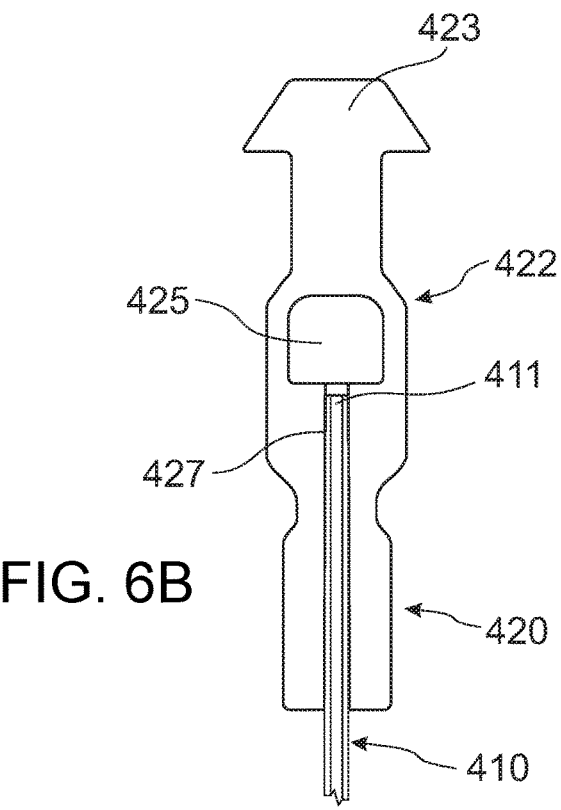
Figure 6C:
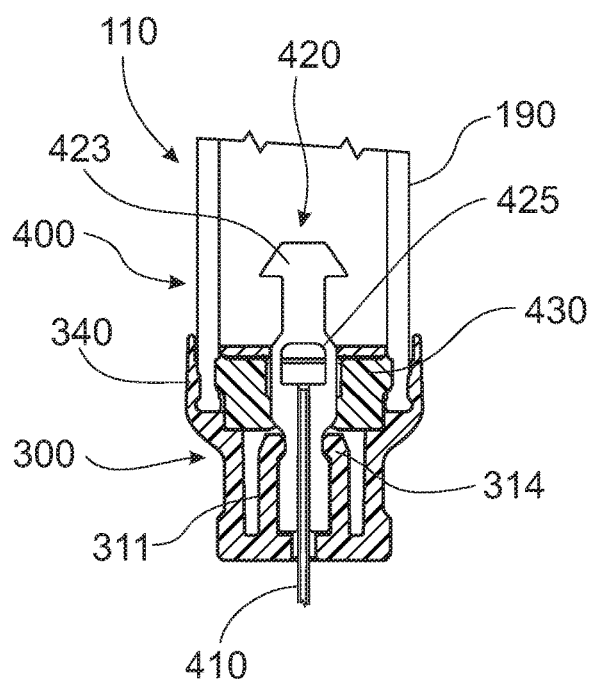

In another embodiment shown in FIG. 6, cannula 410 may be glued into bore 427 in needle body 420. Bore 427 may be drilled, moulded or a combination thereof. As also shown in FIG. 11, extension 340 of barrel-engaging portion 330 of adapter 300 is glued to outside wall 190 of barrel 110, the advantage of which is a relatively shorter assembly length.

Figure 7:
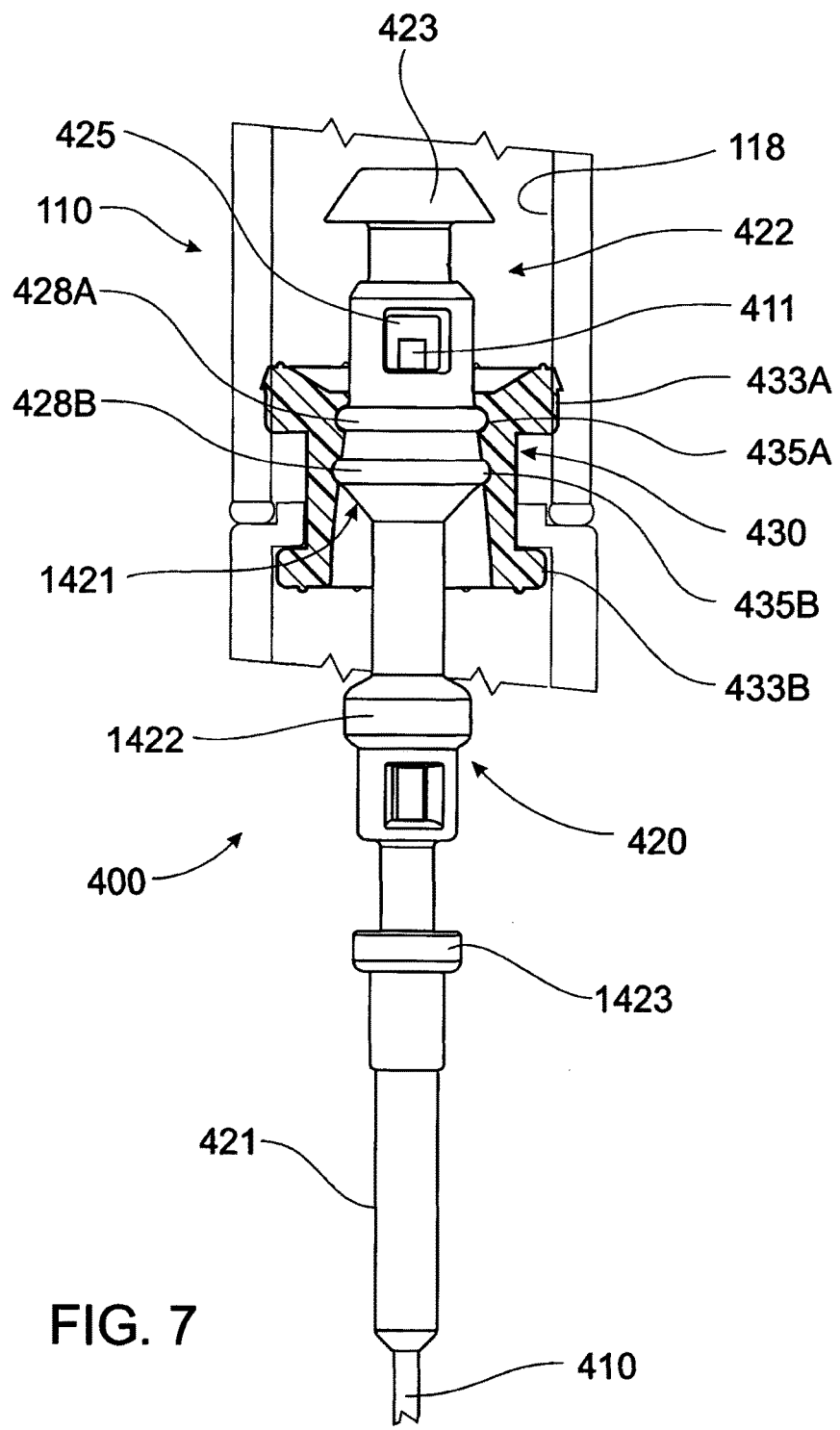
FIG. 7 shows another embodiment of a retractable needle mounted to another embodiment of needle seal.

Another embodiment of retractable needle 400 and needle seal 430 is described in FIG. 7. In this embodiment, retractable needle 400 comprises cannula 410 and needle body 420 comprising elongate portion 421 and proximal end 422 that comprises plunger-engaging member 423, circumferential ribs 428A, B in waist or increased diameter portion 1422 and aperture 425. Needle seal 430 comprises body 431 having sealing ribs 433A, 433B that facilitate a fluid seal against inside wall 118 of barrel 110 and circumferential grooves 435A, B. Circumferential ribs 428A, B of retractable needle 400 releasably engage circumferential grooves 435A, B of needle seal 430 in a manner which facilitates initially holding retractable needle 400 prior to retraction, but facilitates efficient and smooth release of retractable needle 400 from needle seal 430 during retraction.

Figure 8:
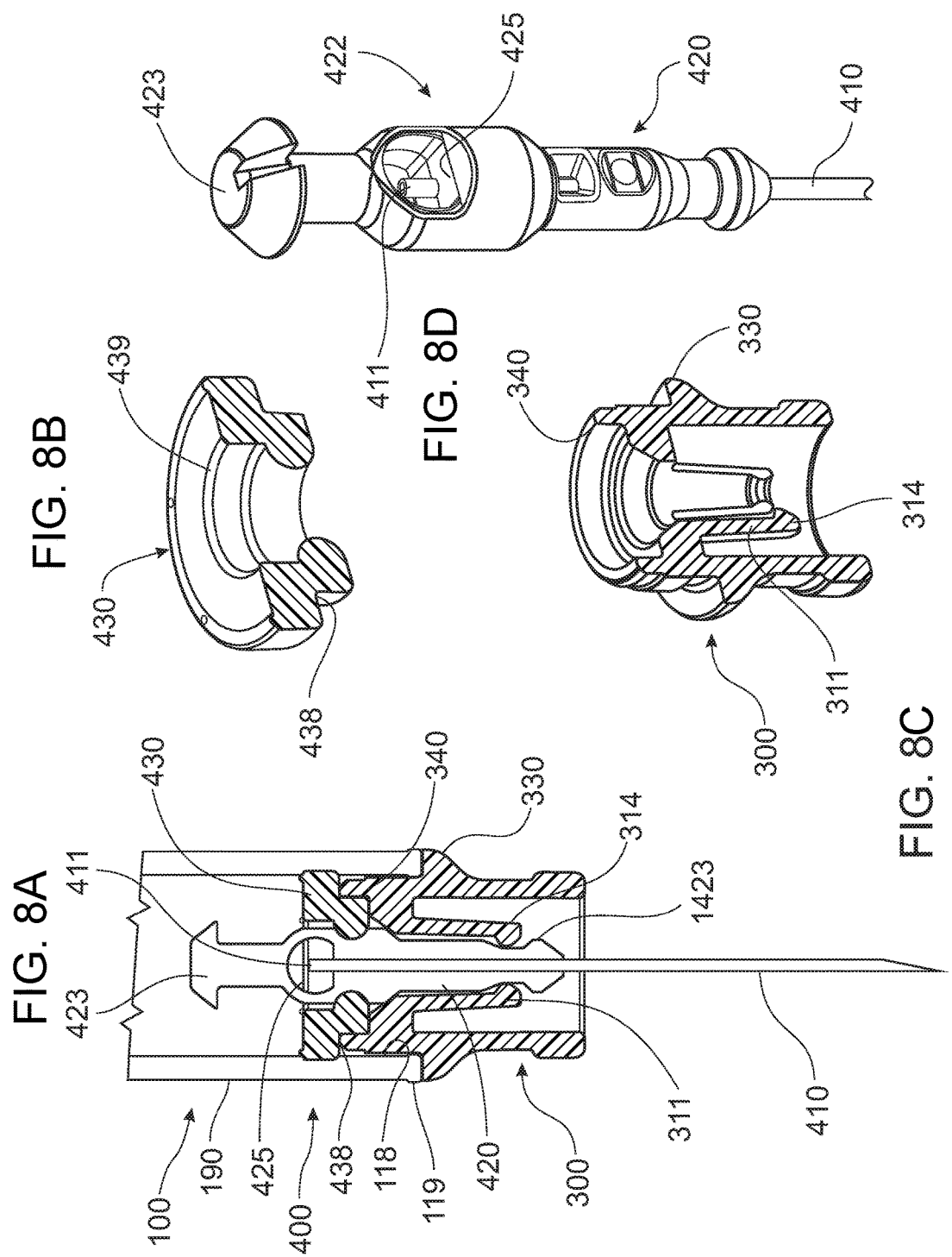
FIGS. 8A, 8B, 8C and 8D show another embodiment of a retractable needle mounted to an embodiment of a barrel adapter and needle seal.
Figure 9:
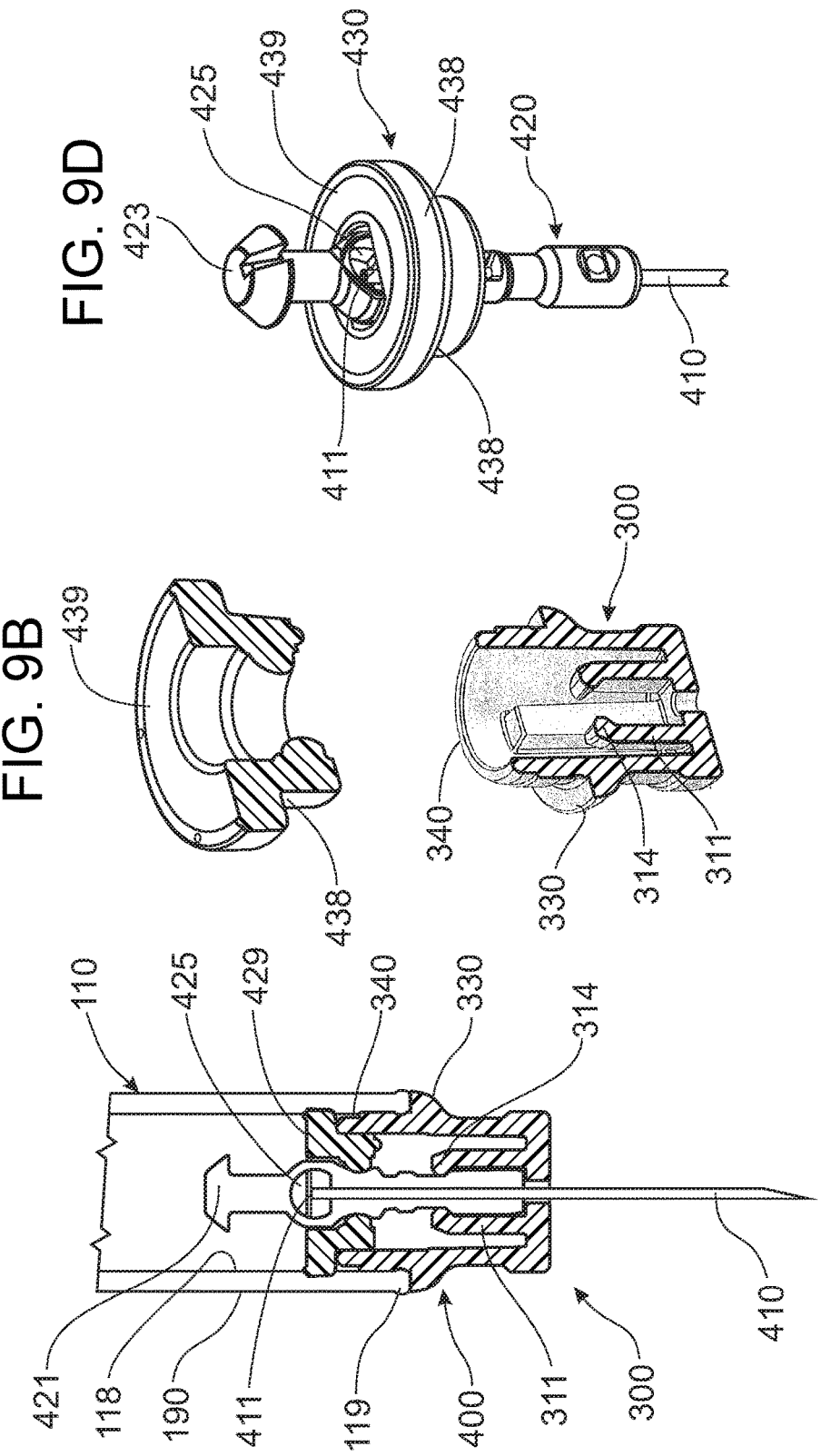
FIGS. 9A, 9B, 9C and 9D show another embodiment of a retractable needle mounted to an embodiment of a barrel adapter and needle seal.
Figure 10:
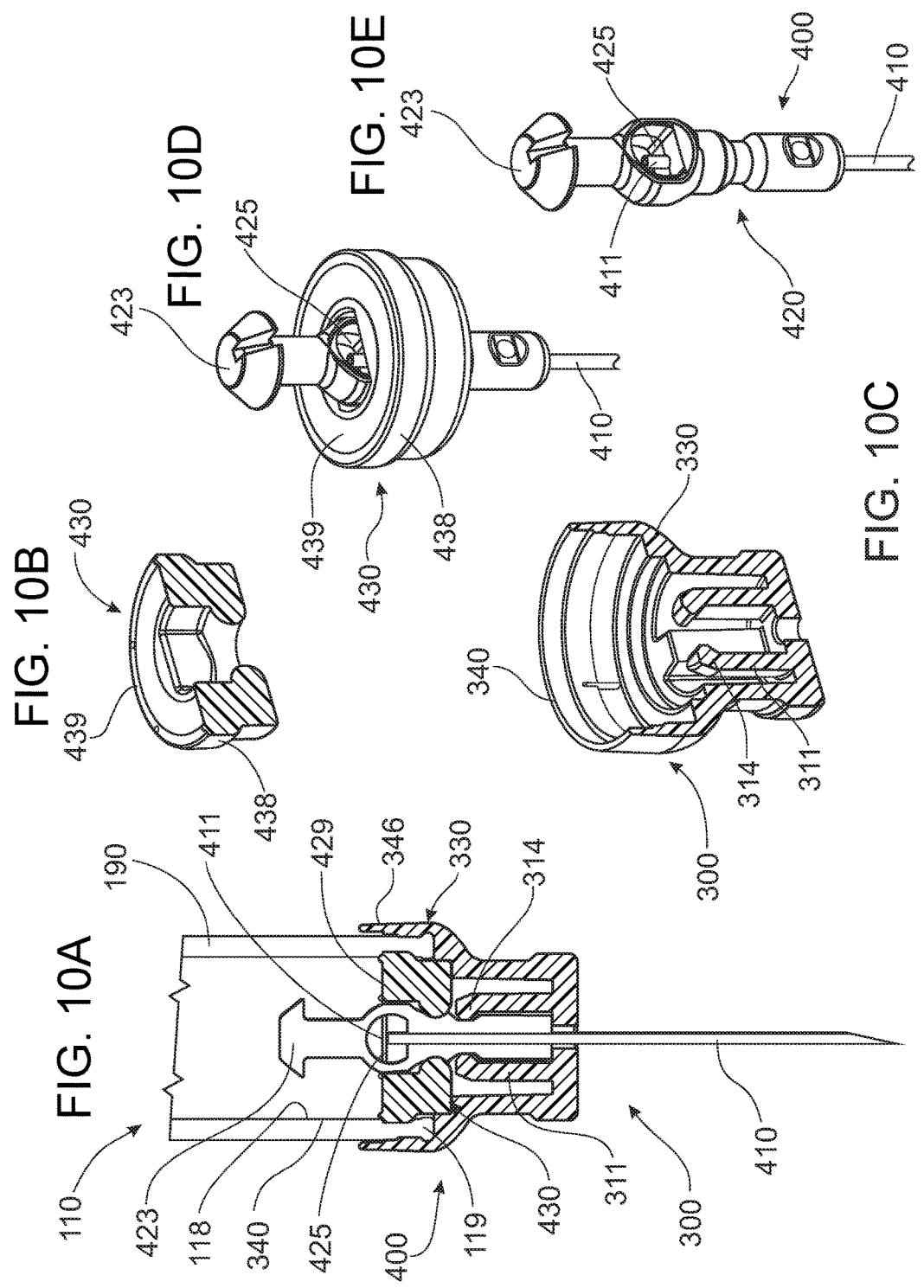
FIGS. 10A, 10B, 10C, 10D and 10E show another embodiment of a retractable needle mounted to an embodiment of a barrel adapter and needle seal.

It will also be appreciated that engagement between adapter 300, needle seal 430 and barrel 110 may be varied. In FIG. 8 and FIG. 10, extension 340 of adapter 300 is glued between inside wall 118 of barrel 110 and needle seal 430. In FIG. 10, extension 340 of barrel-engaging portion 330 of adapter 300 is glued to outside wall 190 of barrel 110, the advantage of which is a relatively shorter assembly length. It will also be appreciated that engagement between barrel adapter 300 and retractable needle body 420 may be varied. In the embodiments shown in FIGS. 2, 6, 9 and 10, spigot 311 projects proximally (i.e., towards the user) but in FIG. 8 a variation is contemplated wherein spigot 311 projects distally (i.e., away from the user) to engage needle body 420.

Figure 11:
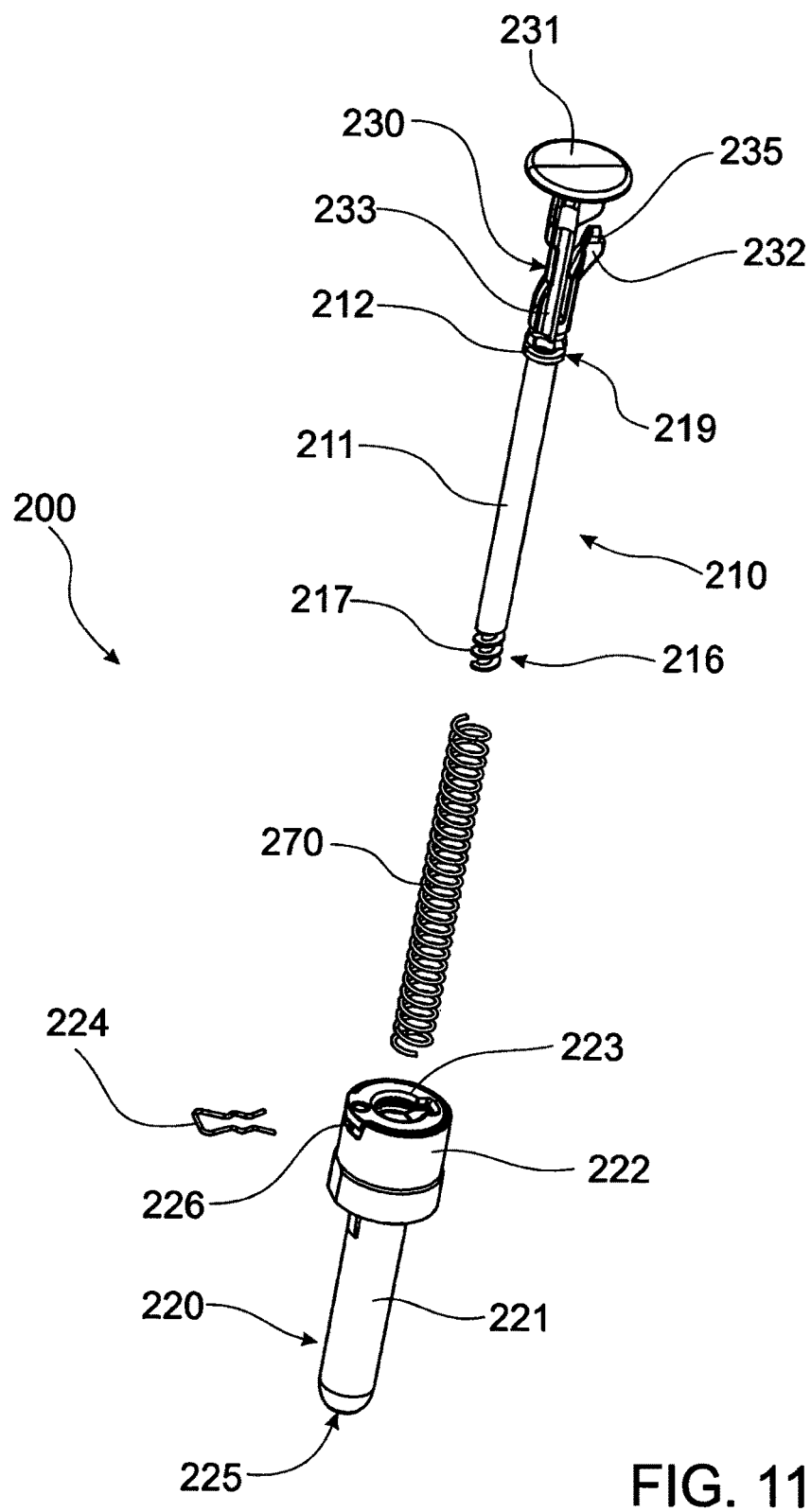
FIG. 11 shows an embodiment of a plunger.
Figure 12:
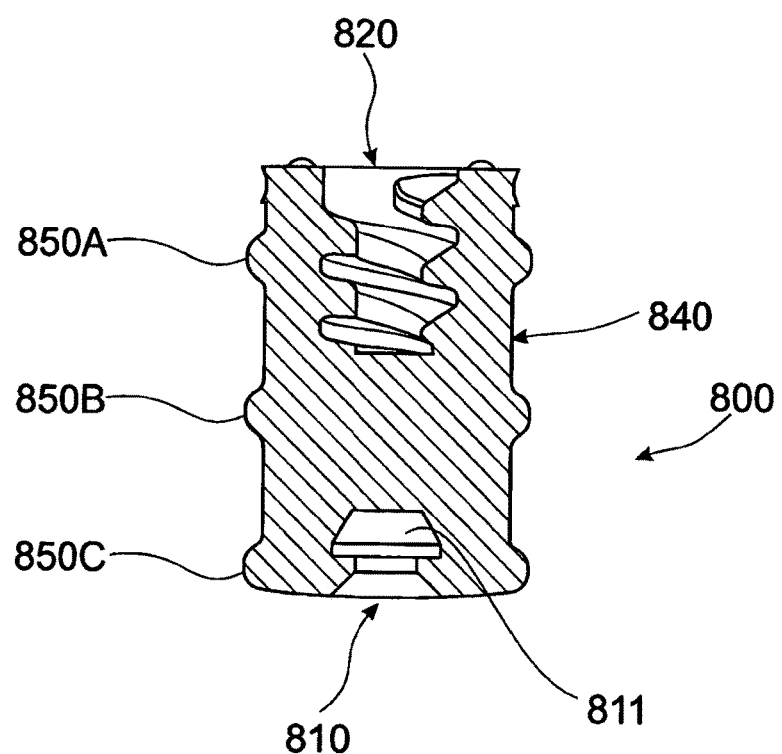
FIG. 12 shows an embodiment of a plunger seal.

Referring particularly to FIG. 11 and FIG. 12, plunger 200 comprises plunger member 210 comprising shaft 211, annular ledge 212 and seal-engaging member 216, which in this embodiment is screw-threaded projection 217, which engages complementary recess 820 of plunger seal 800. In an alternative embodiment, seal-engaging member 216 may be in the form of a snap lock projection that engages a complementary recess in plunger seal 800. Referring particularly to FIG. 12, plunger seal 800 is of unitary construction and comprises seal body 840 and sealing ribs 850A, 850B, 850C that effect a fluid-tight seal between plunger 200 and inside wall 118 of barrel 110. Recess 820 of plunger seal 800 engages complementary seal-engaging member 216 of plunger member 210. In this embodiment, recess 820 comprises a female screw thread 821 that engages male screw-threaded projection 217 of plunger member. Plunger seal 800 further comprises needle-engaging member in the form of recessed seat 810 comprising flange 811 that can receive plunger-engaging member 421 of needle body 420.

Referring particularly to FIG. 11, plunger member 210 further comprises locking groove 219, the function of which will be described in more detail hereinafter. Plunger 200 further comprises plunger outer 220 having elongate body 221 with base 225 and head 222 in which is fitted cap 223. A first locking member comprises lock spring 224 mounted through slot 226 extending through head 222 and cap 223 to thereby assist assembly of plunger 200. Lock spring 224 and locking groove 219 co-operate to lock plunger member 210 and plunger outer 220 together at the end of retraction.

Elongate body 221 further comprises a second locking member comprising a locking finger which has an abutment a described in WO2011/137488. Engagement between the locking finger and release ring 130 of collar 113 is essentially as described in WO2011/137488. Controlling member 230 comprises button 231, arm 232 and shaft 233. Plunger 200 further comprises compressed spring 270 which is mounted between plunger member 210 and plunger outer 220, held in an initially compressed state between annular ledge 212 of plunger member 210 and base 225 of plunger outer 220. Button 231 may have a textured surface to improve feel and grip for a user. Controlling member 230 also releasably engages plunger outer 220 to thereby retain spring 270 in an initially compressed state held between annular ledge 212 of plunger member 210 and base 225 of plunger outer 220. Initially, ledge 235 of arm 232 abuts rim 229 of head 222 of plunger outer 220 to thereby retain controlling member 230 and prevent axial movement of controlling member 230 relative to plunger outer 220. However, arm 232 of controlling member 230 is resiliently flexible and movable out of engagement with controlling member 230 from plunger outer 220 to facilitate decompression of spring 270, similar to that described in WO2011/137488.

The sequence of events whereby retractable needle 400 is disengaged from needle seal 430 to facilitate retraction of retractable needle 400 is as follows. Typically, syringe 100 is provided prefilled with fluid contents for delivery. Therefore, plunger 200 is provided in an initial position ready for depression to deliver the fluid contents of the syringe 100. During delivery of fluid contents, plunger 200 moves axially through barrel 110 in the direction of the solid arrow shown in FIG. 13 until recessed seat 810 of plunger seal 800 has coupled with plunger-engaging member 423, which is barb-like in structure, to thereby couple needle body 420 and plunger member 210.

Plunger 200 continues to move axially so that seal 800 continues to bear against needle seal 430. Needle seal 430 is incapable of axial movement relative to barrel adapter 300, so body 431 of needle seal 430 compresses sufficiently to allow arm 232 of controlling member 230 to contact release ring 130 of collar 113 to thereby disengage ledge 235 of arm 232 from rim 229 of head 222 of plunger outer 220 which allows disengagement of controlling member 230 from plunger outer 220 to facilitate decompression of spring 270 which serves to disengage (pull out) needle body 420 from needle seal 430 for retraction of needle assembly 400 into barrel 110 of syringe 100.

Essentially as described in WO2011/137488, at the end of injection of fluid contents, abutment 228 of locking finger 227 of plunger outer 220 engages underside 131 of release ring 130 to thereby prevent movement of plunger outer 220 out of barrel 110. In order for retractable needle body 420 and cannula 410 coupled to plunger member 210 to retract, compressed spring 270 must decompress, which is facilitated by plunger member 210 disengaging from plunger outer 220. Arm 232 of controlling member 230 bears against release ring 130 of collar 113 at the plunger end 114 of barrel 110. Release ring 130 forces arm 232 to move radially inwardly and out of engagement with rim 229 of head 222 of plunger outer 220. This disengagement allows compressed spring 270 to decompress and push against ledge 212 of plunger member 210 to thereby retract plunger member 210 with controlling member 230 coupled thereto, essentially as described in WO2011/137488. While needle retraction is "automatically" driven by decompression of spring 270, the rate of retraction can be controlled by a user relaxing pressure (such as by way of thumb pressure) against button 231 of controlling member 230.

At the end of retraction of plunger member 210, further movement of plunger member 210 relative to plunger outer 220 and/or barrel 110 is prevented by lock spring 224 "snap locking" around locking groove 219 in plunger member 210. The locking of plunger member 210 at the end of retraction prevents inadvertent removal of plunger member 210 from plunger outer 220 and also prevents inadvertent depression of plunger member 210, both of which would expose cannula tip 411 and thereby expose the user to a potential needle stick injury.

At the end of retraction, controlling member 230 can be manually removed from retractable syringe 100 and discarded as "clean" waste so that there is little if any plunger 220 protruding externally from plunger outer 220 with which to attempt to force plunger 200 back into barrel 110 and attempt to re-engage the needle (not shown).

Figure 13:
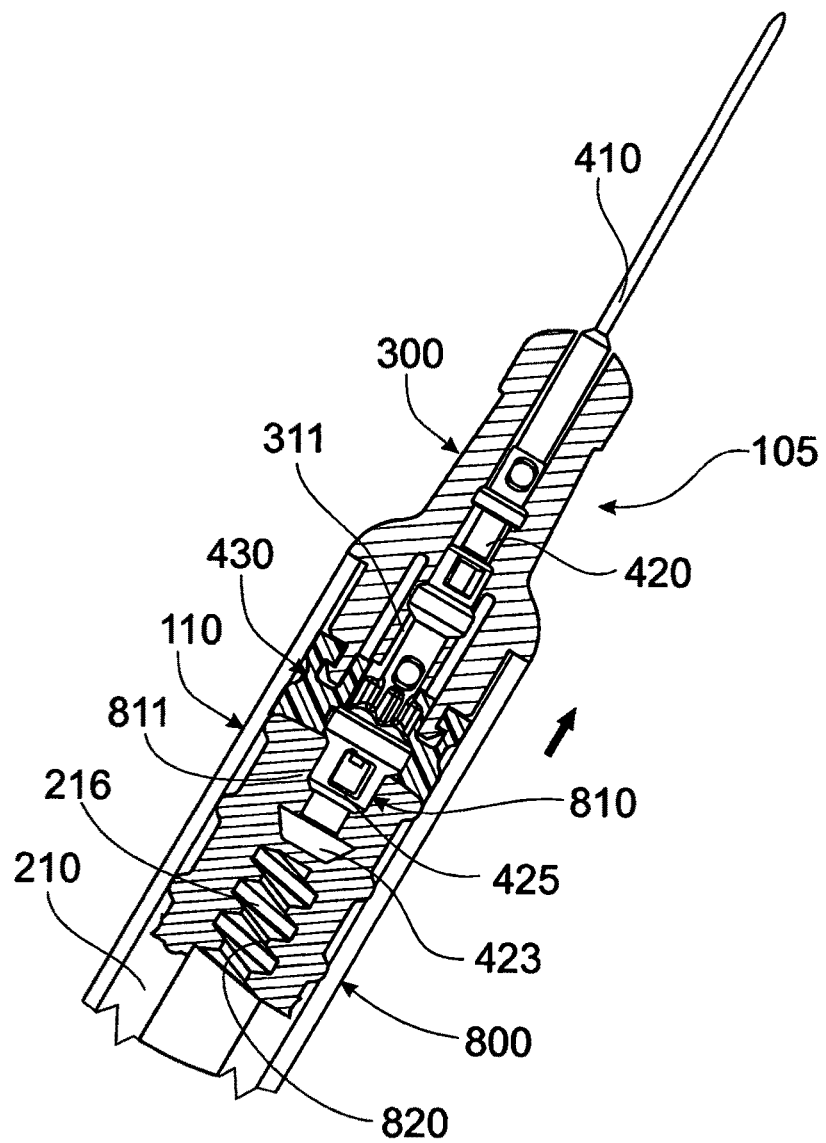
FIG. 13 shows an embodiment of a plunger engaging an embodiment of a retractable needle.
Figures 14A, 14B:
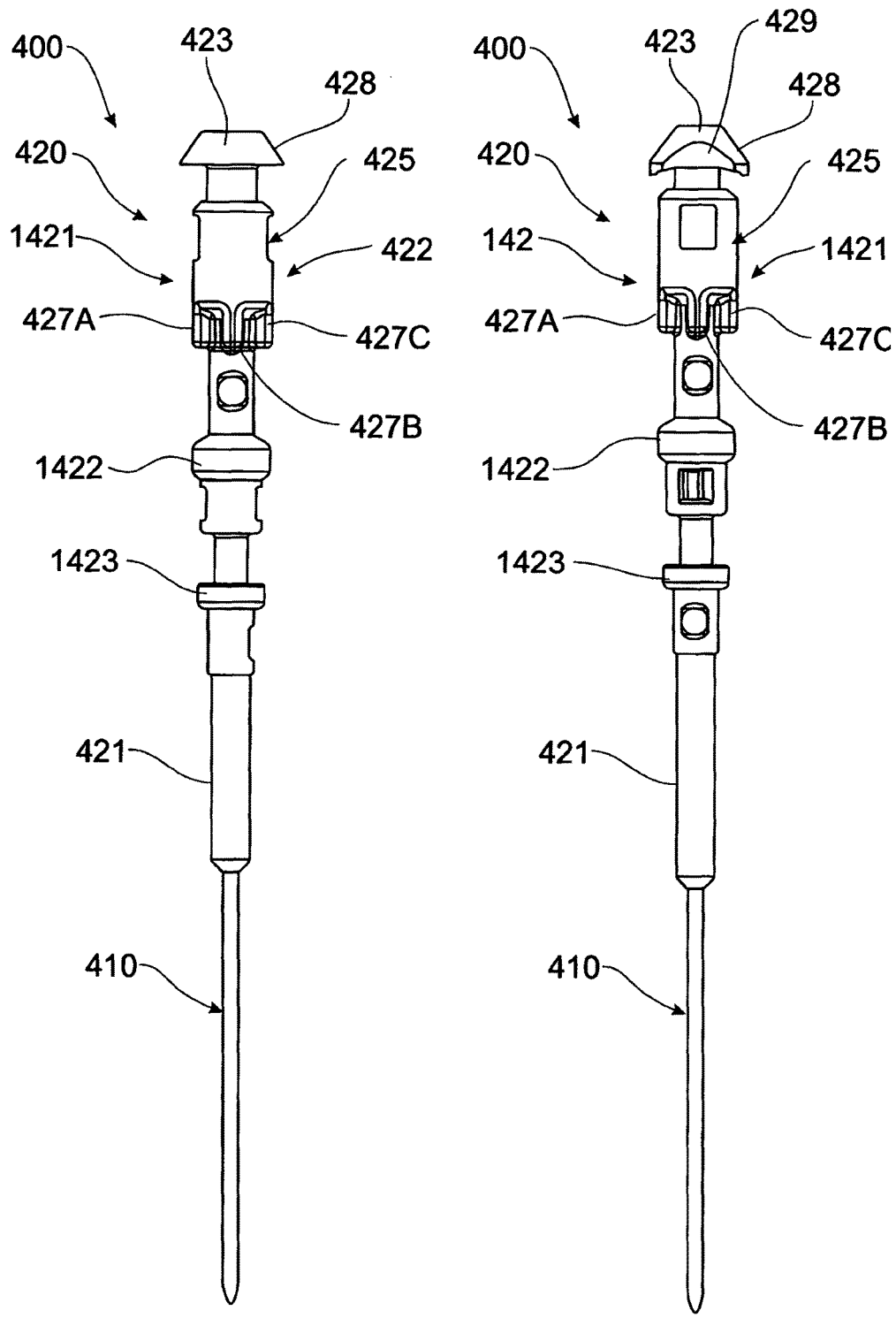
FIG. 14 shows other embodiments of a retractable needle.

The invention also contemplates improved engagement between plunger seal 800 and needle body 420. In FIG. 13 and FIG. 14A, plunger-engaging member 423 is barb-like in structure with sloped shoulder 428. In FIG. 14B, plunger-engaging member 423 is barb-like in structure but with chamfered surfaces 429 to reduce the force required for plunger seal 800 to engage and "capture" and plunger-engaging member 423 prior to needle retraction.

Figure 15A:
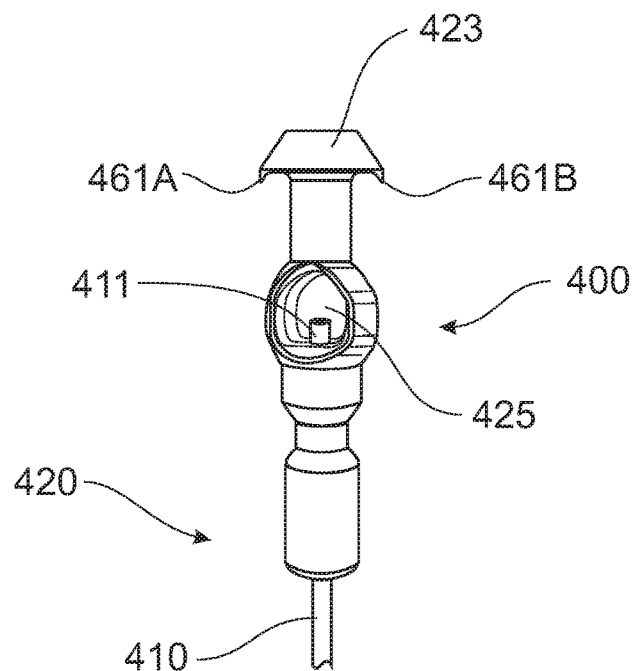
FIGS. 15A and 15B show an embodiment of a plunger-engaging member of a retractable needle.
Figure 15B:
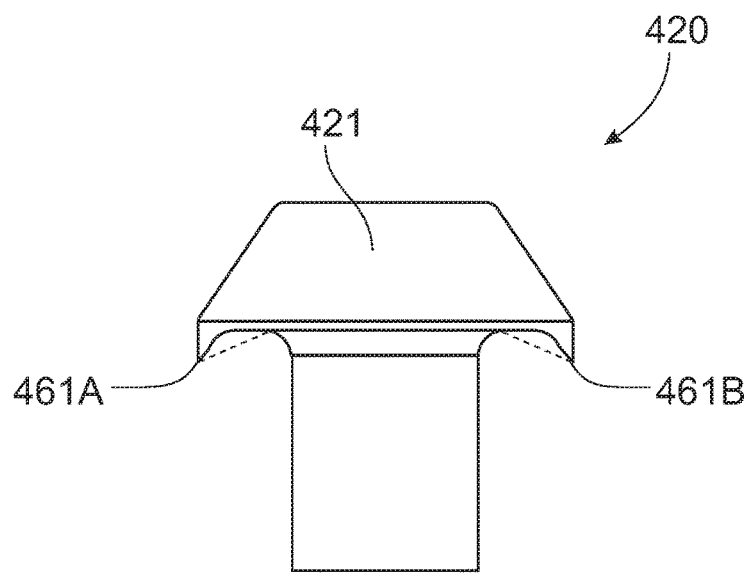

In one embodiment shown in FIG. 15, needle body 420 comprises plunger engaging member 423 that comprises hook ends 461A, B that may more effectively engage plunger seal 800 (which is typically formed of rubber) by "digging into" or "grabbing" plunger seal 800 when engaged therewith.

In another embodiment shown in FIG. 16, needle body 420 comprises plunger-engaging member 423 that comprises resilient, flexible arms 461 A, B. Plunger seal 800 comprises needle-engaging member 810 which receives and engages flexible arms 461A, B, wherein flexible arms 461 A, B effectively pivot radially inwardly (as indicated by the hatched arrows) to enter neck cavity 811 of needle-engaging member 810 and then pivot radially outwardly once in head cavity 812 of needle-engaging member 810 of needle-engaging member 810. Flexible arms 461 A, B respectively comprise sharp edges 462 A, B that effectively engage plunger seal 1800 (which is typically formed of rubber) by "digging into" inside wall 813 of head cavity 812.

It will also be appreciated that the axial positioning of needle-engaging member 810 in plunger seal 800 may be chosen to reduce the amount of force exerted by the user (e.g., Peak User Force or "PUF"). Typically, the more distal to the user is needle-engaging member 810 located in plunger seal 800, the earlier it will engage needle body 420. Accordingly, the skilled person .may more effectively temporally separate (i) needle body 420 engagement with plunger seal 800 and (ii) release of plunger outer 220 and controlling member 230 to allow decompression of spring 70 (as hereinbefore described), by ensuring a suitably distal location of needle-engaging member 810 in plunger seal 800. This ensures that both (i) and (ii) do not occur simultaneously (in which case the total peak user force is the sum of the forces required for (i) and (ii)), but instead occur sequentially, thereby reducing the total PUF: Suitably, needle body 420 engagement with plunger seal 800 occurs slightly before release of plunger outer 220 and controlling member 230, so that the needle body 420 is fully engaged by plunger seal 800 before retraction can occur.

Typically, as shown in FIG. 1, glass barrel 110 is substantially cylindrical in shape however the invention could be practiced in relation to any glass barrel shape. In one embodiment, barrel 110 has an elliptical cross-section to prevent rotation of plunger seal 800, thereby facilitating a more reliable threading engagement between plunger seal 800 and plunger member 210. An elliptical barrel 110 would facilitate machine screwing of plunger member 210 into plunger seal 800 set with a torsion clutch, in which case every plunger member 210 would screw in with the same torsion because the plunger seal 800 would always be stopped from rotating in elliptical barrel 110, so at a pre-set force, the driver would stop and every assembly would be the same. This embodiment also contemplates elliptical barrel 110 and plunger seal 800 with an elliptical shape. By way of example, it may be possible to heat and slightly flatten barrel 110 to provide a very small degree of ellipse, so that plunger seal 800 keeps its sealing function during the threading process.

In relation to glass barrels 110 generally, manufacturing tolerances over the length of a glass barrel are +/−0.5 mm, which is much larger than plastic injection moulding where axial tolerances of +/−0.1 mm are achievable. This may be problematic with retractable syringe 100 because the timing of retraction activation is critical for safe retraction. The issues are that:

(a) The medication dose must always be fully delivered, with minimal dead space, before retraction;

(b) The plunger seal 800 must fully engage and capture needle body 420 before retraction spring 270 decompresses;

(c) The needle body 420 should always be engaged by plunger seal 800 to ensure it is retracted with plunger 200 when retraction occurs (e.g. no more than 4 failures in 1,000,000 injections would be commercially acceptable);

(d) The engagement of the needle body 420 by the plunger seal 800 occurs at the needle end 105 of barrel 110 whereas the release of the spring by arm 232 contacting release ring 130 occurs at plunger end 104 of barrel 110. With the glass barrel tolerance being +/−0.5 mL, the timing of these two actions is difficult to control.

An embodiment of the invention provides a solution to the glass tolerance problem. According to this embodiment, collar 113 comprising release ring 130 and barrel adapter 300 are glued to glass barrel 110 using jigs and fixtures to set a fixed distance between collar 113 and adapter 300 with a tolerance of +/−0.05 mm, thereby overcoming the larger glass barrel tolerance.

Certain embodiments of the invention also address problems relating to activation of spring 270 decompression. In prior art retractable syringes such as described in WO2011/137488, while spring 270 is initially compressed within plunger 200, there is further compression of spring 270 towards the end of plunger 200 depression after engagement of needle body 420 just prior to activation of spring 270 decompression and needle 400 retraction. This further spring 270 compression occurs as release ring 130 moves arm 232 of controlling member 230 radially inwardly and out of engagement with rim 229 of head 222 of plunger outer 220. The movement of arm 232 by release ring involves some angled, "upward" or proximal movement (i.e toward the user) of ledge 235 which requires further, axial compression of spring 270.

This additional compression of spring 270 requires additional force to be applied by a user.

FIG. 17 shows embodiments of a solution to this problem by eliminating or decreasing the angled, "upward" or proximal movement described above, replaced by an essentially lateral movement of tang 295 to facilitate release of controlling member 230 and plunger outer 220 and allow spring 270 (not shown) to decompress. This entirely lateral movement to trigger disengagement prevents further axial travel of controlling member 230 and further compression of retraction spring 270.

In one embodiment, tang 295 is connected to controlling member 1230 by intermediate biasing member 297, which in this embodiment is a coil spring. Angled face 296 of tang 295 bears against release ring 130 and moves laterally against spring 297 in the direction of the solid arrow out of engagement with head 222 of plunger outer 220.

In another embodiment, tang 295 is a component of head 222 of plunger outer 220 and initially engages recess 298 of controlling member 230. Release ring 130 bears against head 222 thereby moving tang 295 laterally out of engagement with recess 298 of controlling member 230 in the direction of the solid arrow. In this embodiment, tang 295 is hingedly connected to head 222 so that tang 295 can move laterally out of engagement with recess 298 of controlling member 230.

Figure 18A:
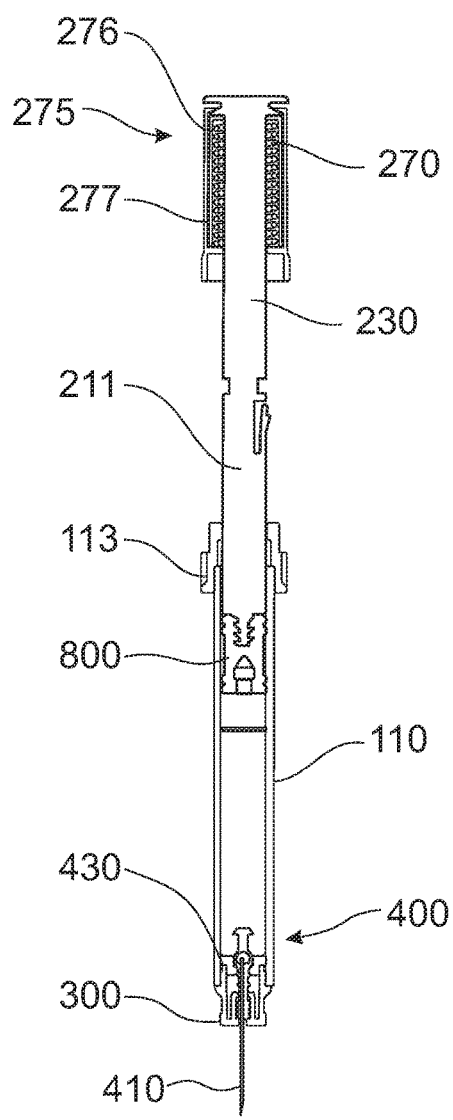
FIGS. 18A and 18B show an embodiment of a spring retainer mounted to plunger.
Figure 18B:
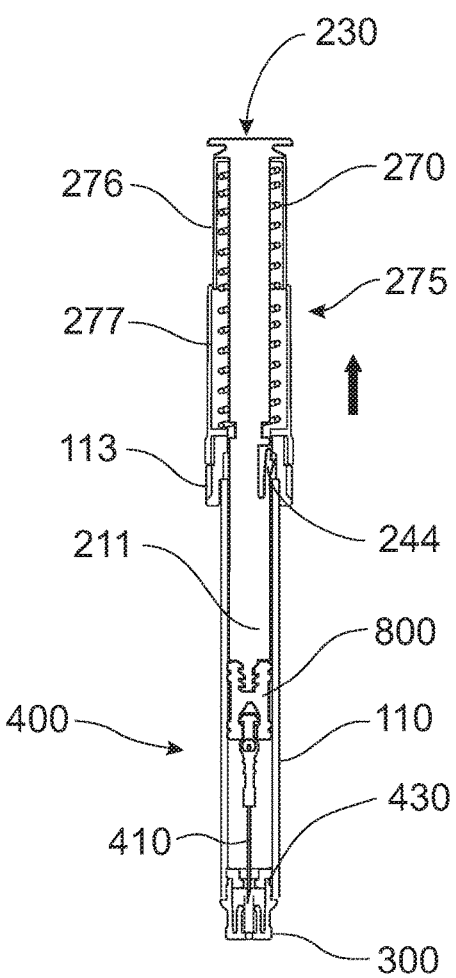

Referring to FIG. 18, the invention also provides an embodiment where spring 270 is located in a retainer 275 comprising inner member 276 and outer member 277 which, in an initially engaged form, retain spring 270 in a compressed state. Retainer 275 is mounted to controlling member 230 and at the end of depression of plunger 200, inner member 276 and outer member 277 axially disengage to enable decompression of spring 270 to retract controlling member 230 and plunger member 210 with needle 400 coupled thereto. Inner member 276 travels axially and proximally (L e. towards a user) with retracting controlling member 230 in the direction of the solid arrow and eventually interlocks with outer member 277. Locking arm 244 of plunger member 210 locks under collar 113 to prevent plunger 200 being withdrawn from barrel 110. This embodiment can allow the use of a larger retraction spring 270 than would be used in the embodiment shown in FIG. 6 of WO2011/137488, for example. Furthermore, plunger inner member 210 can be relatively increased in diameter (e.g compared to that in FIG. 6 of WO2011/137488) because there is no need to provide space for retraction spring 270 between plunger member 210 and plunger outer 220. Thus, plunger member 210 may be a "snug" fit in barrel 110, thereby reducing plunger member 210 wobble and increasing stability while assisting the incorporation of a "lock-out" tab and prevention of "shooting".

Another embodiment of plunger 200 is contemplated wherein plunger member 210 further comprises a flange on shaft 211 that abuts plunger seal 800 and acts to reduce plunger member 210 wobble and tilt during axial movement of plunger 200. The flange would also act to prevent "shooting" of plunger member 210.

In light of the foregoing, it will be appreciated that the invention provides the invention provides an improved retractable needle which facilitates delivery of the fluid contents of a retractable syringe. The retractable needle aperture is positioned to maximize the efficiency of fluid delivery. and eliminates the visual "dead volume" associated with many retractable syringes. Furthermore, the retractable needle having an aperture permits accurate dose control by users by eliminating the visual bubble commonly found in the known syringes.

Also, the retractable needle and collar are already fitted to the syringe barrel, allowing a pharmaceutical company to fill the barrel in the normal filling production line without any modifications required.

Furthermore, other embodiments of the invention provide an improved plunger that displays less wobble and/or tilt during axial movement, an improved needle assembly whereby fluid wastage is minimized, improved coupling between needle and plunger seal, an improved coupling between plunger seal and plunger, improved plunger lockout to prevent syringe re-use and/or improved systems for housing an initially compressed spring and/or activation of spring decompression, although without limitation thereto.

Each of the embodiments described herein may be used alone or in combination with one or more other embodiments in a retractable syringe.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A needle assembly comprising a retractable needle and a needle seal, the needle assembly mountable to a barrel of a syringe comprising a plunger including a portion capable of engaging the retractable needle for retraction of the retractable needle, the retractable needle comprising: a cannula; a needle body having an elongate portion which houses at least part of the cannula, a plunger-engaging member, and at least one aperture located between the plunger-engaging member and the elongate portion, the at least one aperture extending transversely through the needle body relative to a longitudinal axis of the cannula, the at least one aperture being locatable in fluid communication with fluid contents of the syringe barrel; the cannula comprising a proximal end which is in fluid communication with, and extends into, the at least one aperture; the needle seal releasably mounted to the retractable needle so that the proximal end of the cannula is positioned distal to a proximal edge of the needle seal to thereby eliminate bubbles and minimize dead space.

2. The needle assembly of claim 1, wherein the needle seal comprises at least one mating portion capable of engaging at least one complementary mating portion of the retractable needle.

3. The needle assembly of claim 2, wherein the mating portions are grooves capable of releasably engaging ribs of the needle body.

4. The needle assembly of claim 1, which is mountable to a syringe barrel adapter comprising a body that includes a needle portion and a barrel-engaging portion.

5. A retractable syringe comprising a barrel, the needle assembly of claim 1 mounted to the barrel and a plunger comprising a portion capable of engaging the plunger-engaging member of the retractable needle.

6. The retractable syringe of claim 5, wherein the needle assembly is mounted to a syringe barrel adapter comprising a body that includes a needle portion and a barrel-engaging, portion.

7. The retractable syringe of claim 5, wherein the plunger comprises a plunger member, a plunger outer, a controlling member and biasing means, wherein the plunger member, the plunger outer and the controlling, member co-operate to retain the biasing means in an initially energized state.

8. The retractable syringe of claim 7, wherein the biasing member is a spring.

9. The retractable syringe of claim 5, which is a prefilled retractable syringe.

10. The needle assembly of claim 1, which is unitary.

11. The needle assembly of claim 10, wherein the cannula and the needle body are co-molded to form the unitary retractable needle.

12. The needle assembly of claim 1, wherein the needle body and the cannula are separate components of the retractable needle.

13. The needle assembly of claim 12, wherein the needle body is an overmold of the cannula.

14. The needle assembly of claim 12, wherein the needle body comprises a first body member and a second body member.

15. The needle assembly of claim 13, wherein, prior to assembly, the first body member comprises the cannula and the second body member comprises the plunger-engaging member.

16. The needle assembly of claim 1, wherein the plunger-engaging member comprises at least one chamfered surface.

17. The needle assembly of claim 1, wherein the plunger-engaging member comprises at least one hook portion capable of engaging a portion of the plunger capable of engaging the plunger-engaging member.

18. The retractable needle of claim 1, wherein the at least one aperture is disposed at least partially proximal to the needle seal.

19. The retractable needle of claim 1, wherein the proximal end of the cannula opens directly into the at least one aperture.

20. The retractable needle of claim 19, wherein the proximal end of the cannula extends proximal to or terminates at a distal edge of the at least one aperture.

\* \* \* \* \*